US00PP23297P2

(12) United States Plant Patent
Misato

(10) Patent No.: US PP23,297 P2
(45) Date of Patent: Jan. 1, 2013

(54) ***VERBENA* PLANT NAMED 'SUNTAPIRIPI'**

(50) Latin Name: *Verbena×hybrida*
Varietal Denomination: Suntapiripi

(75) Inventor: Tomoya Misato, Shiga (JP)

(73) Assignee: Suntory Flowers Ltd., Tokyo (JP)

( * ) Notice: Subject to any disclaimer, the term of this patent is extended or adjusted under 35 U.S.C. 154(b) by 97 days.

(21) Appl. No.: 13/065,247

(22) Filed: Mar. 17, 2011

(51) Int. Cl.
*A01H 5/00* (2006.01)

(52) U.S. Cl. ..... Plt./308

(58) Field of Classification Search ..... Plt./308
See application file for complete search history.

*Primary Examiner* — June Hwu
(74) *Attorney, Agent, or Firm* — C. A. Whealy

(57) ABSTRACT

A new and distinct cultivar of *Verbena* plant named 'Suntapiripi', characterized by its trailing plant habit; vigorous growth habit; freely branching habit; early and freely flowering habit; and light purple-colored flowers held above and beyond the foliar plane.

1 Drawing Sheet

Botanical designation: *Verbena×hybrida.*
Cultivar denomination: 'SUNTAPIRIPI'.

BACKGROUND OF THE INVENTION

The present invention relates to a new and distinct cultivar of *Verbena* plant, botanically known as *Verbena×hybrida*, and hereinafter referred to by the name 'Suntapiripi'.

The new *Verbena* plant is a product of a planned breeding program conducted by the Inventor in Higashiomi, Shiga, Japan. The objective of the breeding program is to create new compact and freely branching *Verbena* plants with trailing plant habit and attractive flower coloration.

The new *Verbena* plant originated from a cross-pollination made by the Inventor in November, 2007 in Higashiomi, Shiga, Japan of a proprietary selection of *Verbena×hybrida* identified as code number T04-7-1, not patented, as the female, or seed, parent with a proprietary selection of *Verbena×hybrida* identified as code number T93, not patented, as the male, or pollen, parent. The new *Verbena* plant was discovered and selected by the Inventor as a single flowering plant within the progeny of the stated cross-pollination in a controlled environment in Higashiomi, Shiga, Japan in October, 2008.

Asexual reproduction of the new *Verbena* plant by cuttings in a controlled environment in Higashiomi, Shiga, Japan since November, 2008 has shown that the unique features of this new *Verbena* plant are stable and reproduced true to type in successive generations.

SUMMARY OF THE INVENTION

Plants of the new *Verbena* have not been observed under all possible environmental conditions and cultural practices. The phenotype may vary somewhat with variations in environment conditions such as temperature and light intensity without, however, any variance in genotype.

The following traits have been repeatedly observed and are determined to be the unique characteristics of 'Suntapiripi'. These characteristics in combination distinguish 'Suntapiripi' as a new and distinct *Verbena* plant:

1. Trailing plant habit.
2. Vigorous growth habit.
3. Freely branching habit.
4. Early and freely flowering habit.
5. Light purple-colored flowers held above and beyond the foliar plane.

Plants of the new *Verbena* can be compared to plants of the female parent selection. Plants of the new *Verbena* differ primarily from plants of the female parent selection in the following characteristics:

1. Plants of the new *Verbena* are more trailing than pants of the female parent selection.
2. Plants of the new *Verbena* and the female parent selection differ in flower color as plants of the female parent selection have darker-colored flowers.

Plants of the new *Verbena* can be compared to plants of the male parent selection. Plants of the new *Verbena* differ primarily from plants of the male parent selection in flower color as plants of the male parent selection have violet-colored flowers.

Plants of the new *Verbena* can be compared to plants of the *Verbena×hybrida* 'Sunmaref TP-P', disclosed in U.S. Plant Pat. No. 9,014. In side-by-side comparisons conducted in Higashiomi, Shiga, Japan, plants of the new *Verbena* differed primarily from plants of 'Sunmaref TP-P' in the following characteristics:

1. Plants of the new *Verbena* were shorter and more trailing than plants of 'Sunmaref TP-P'.
2. Plants of the new *Verbena* had larger inflorescences than plants of 'Sunmaref TP-P'.
3. Plants of the new *Verbena* had shorter peduncles than plants of 'Sunmaref TP-P'.
4. Plants of the new *Verbena* and 'Sunmaref TP-P' differed in flower color as plants of 'Sunmaref TP-P' had light red purple-colored flowers.

BRIEF DESCRIPTION OF THE PHOTOGRAPHS

The accompanying colored photographs illustrate the overall appearance of the new *Verbena* plant showing the colors as true as it is reasonably possible to obtain in colored reproductions of this type. Colors in the photographs may differ slightly from the color values cited in the detailed botanical description which accurately describe the colors of the new *Verbena* plant.

The photograph at the top of the sheet comprises a side perspective view of a typical flowering plant of 'Suntapiripi' grown in a container.

The photograph at the bottom of the sheet is a close-up view of a typical flowering plant of 'Suntapiripi'.

DETAILED BOTANICAL DESCRIPTION

The aforementioned photographs and following observations and measurements describe plants grown during the summer in 15-cm containers in an outdoor nursery in Higashiomi, Shiga, Japan under commercial practices. During the production of the plants, day temperatures averaged 23° C. and night temperatures averaged 13° C. Plants were four months old when the photographs and description were taken. In the following description, color references are made to The Royal Horticultural Society Colour Chart, 2001 Edition, except where general terms of ordinary dictionary significance are used.

Botanical classification: *Verbena×hybrida* 'Suntapiripi'.

Parentage:

*Female, or seed, parent*.—Proprietary selection of *Verbena×hybrida* identified as code number T04-7-1, not patented.

*Male, or pollen, parent*.—Proprietary selection of *Verbena×hybrida* identified as code number T93, not patented.

Propagation:

*Type*.—By cuttings.

*Time to initiate roots*.—About 10 to 14 days at 20° C. to 25° C.

*Time to produce a rooted young plant*.—About four weeks at 20° C. to 25° C.

*Root description*.—Fibrous; white in color.

*Rooting habit*.—Freely branching.

Plant description:

*Plant and growth habit*.—Trailing growth habit; lateral branches decumbent; freely branching habit, pinching enhances lateral branch development; vigorous growth habit.

*Plant height*.—About 7 cm.

*Plant diameter*.—About 59.2 cm.

Lateral branch description:

*Length*.—About 32.2 cm.

*Diameter*.—About 1.9 mm.

*Internode length*.—About 2.3 cm.

*Strength*.—Strong; flexible.

*Texture*.—Pubescent.

*Color*.—Close to 144A.

Foliage description:

*Arrangement*.—Opposite, simple.

*Length*.—About 2.9 cm.

*Width*.—About 3.2 cm.

*Shape*.—Pinnately parted.

*Apex*.—Acute.

*Base*.—Cuneate.

*Margin*.—Pinnately cleft.

*Texture, upper and lower surfaces*.—Pubescent.

*Venation pattern*.—Pinnate; reticulate.

*Color*.—Developing leaves, upper surface: Close to 137C. Developing leaves, lower surface: Close to 144B. Fully expanded leaves, upper surface: Close to 137B; venation, close to 145B. Fully expanded leaves, lower surface: Close to 138B; venation, close to 145B.

*Petiole*.—Length: About 10.4 mm. Diameter: About 1.3 mm. Texture, upper and lower surfaces: Pubescent. Color, upper and lower surfaces: Close to 145B.

Flower description:

*Flower arrangement and habit*.—Salverform flowers arranged in hemispherical terminal racemes; flowers face mostly upright; flowers sessile; freely flowering habit with about twelve flowers per inflorescence and about 49 inflorescences developing per plant.

*Natural flowering season*.—Plants flower continuously from spring to late autumn in Japan; plants begin flowering about four weeks after planting.

*Flower longevity*.—Flowers last about one week on the plant; flowers not persistent.

*Fragrance*.—Slightly fragrant; pleasant.

*Inflorescence diameter*.—About 4.7 cm.

*Flowers*.—Appearance: Flared trumpet, corolla fused, five-parted. Diameter: About 1.8 cm. Depth (height): About 1.7 cm. Tube length: About 1.5 cm. Tube diameter: About 1 mm.

*Flower buds*.—Length: About 1.2 cm. Diameter: About 2.3 mm. Shape: Clavate. Color: Close to 77B.

*Corolla*.—Arrangement: Single whorl of five fused petals. Petal length: About 8.7 mm. Petal width: About 7.4 mm. Petal lobe shape: Cordate. Petal lobe apex: Cordate. Petal lobe margin: Entire. Petal texture, upper and lower surfaces: Smooth, glabrous. Color: Petal, when opening, upper surface: Close to N78B. Petal, when opening, lower surface: Close to N78D. Petal, fully opened, upper surface: Close to N78C. Petal, fully opened, lower surface: Close to 77C. Throat: Close to 145D. Tube: Close to 145D tinged with red.

*Calyx*.—Arrangement: One single narrow calyx tube per flower with five fused sepals. Sepal length: About 1.5 mm. Sepal width: About 1.1 mm. Sepal shape: Triangular. Sepal apex: Acute. Sepal margin: Entire. Sepal texture, upper and lower surfaces: Pubescent. Sepal color, upper and lower surfaces: Close to 144B.

*Peduncles*.—Length: About 3.9 cm. Diameter: About 1.6 mm. Strength: Strong; flexible. Texture: Pubescent. Color: Close to 144A.

*Reproductive organs*.—Stamens: Quantity/arrangement: Four per flower, adnate to corolla tube. Anther shape: Ellipsoidal. Anther size: About 0.9 mm by 0.4 mm. Anther color: Close to 150B. Pollen amount: Scarce. Pistils: Quantity: One per flower. Pistil length: About 11.3 mm. Stigma shape: Bi-parted. Stigma color: Close to 144B. Style color: Close to 145C. Ovary color: Close to 145B. Fruits/seed: Fruit and seed development have not been observed.

Temperature tolerance: Plants of the new *Verbena* have been observed to tolerate temperatures from about 0° C. to about 35° C.

Pathogen/pest resistance: Plants of the new *Verbena* have not been observed to be resistant to pathogens and pests common to *Verbena* plants.

It is claimed:

1. A new and distinct *Verbena* plant named 'Suntapiripi' as illustrated and described.

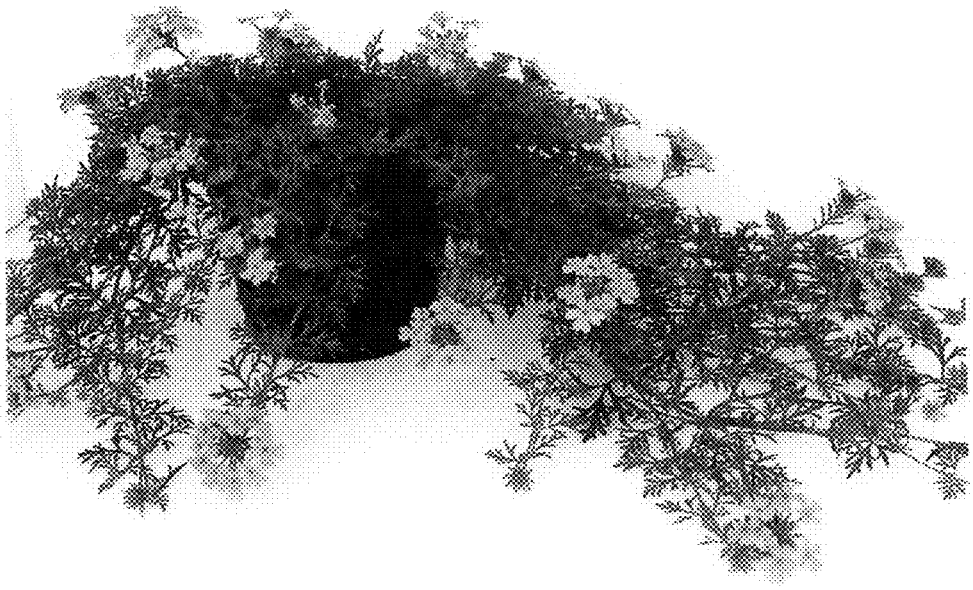
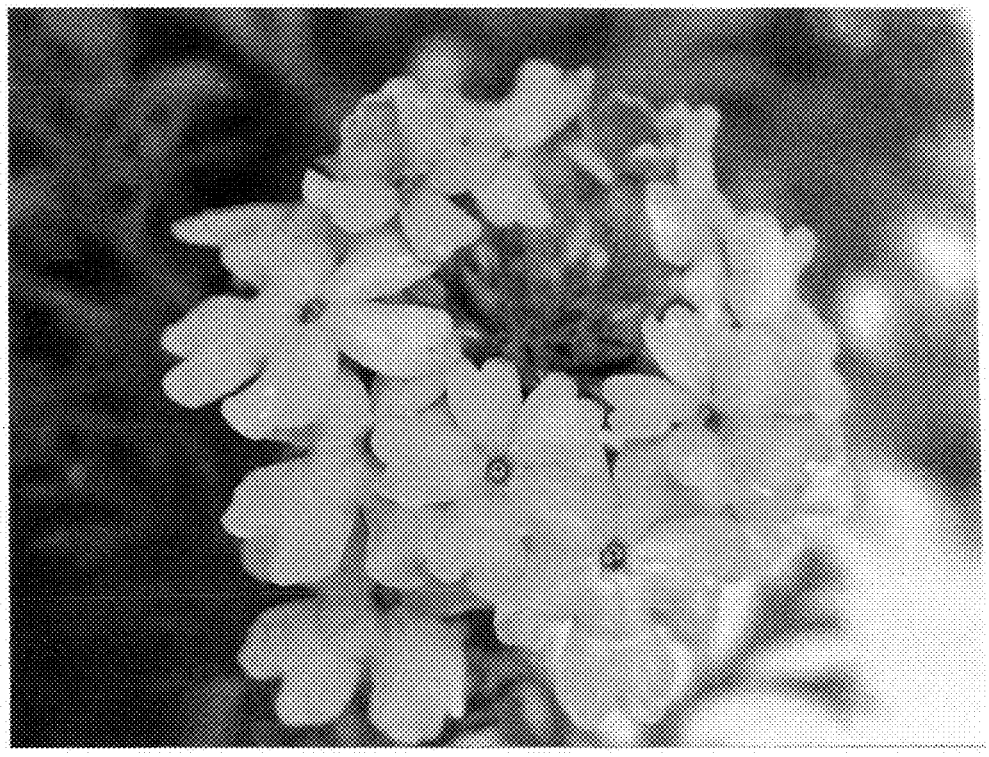

* * * * *